(12) United States Patent
Papas

(10) Patent No.: US 12,016,973 B2
(45) Date of Patent: Jun. 25, 2024

(54) METHODS AND SYSTEMS FOR AUGMENTING IMMUNE SYSTEM RESPONSES

(71) Applicant: ARIZONA BOARD OF REGENTS ON BEHALF OF THE UNIVERSITY OF ARIZONA, Tucson, AZ (US)

(72) Inventor: Klearchos K. Papas, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 848 days.

(21) Appl. No.: 16/339,674

(22) PCT Filed: Oct. 5, 2017

(86) PCT No.: PCT/US2017/055334
§ 371 (c)(1),
(2) Date: Apr. 4, 2019

(87) PCT Pub. No.: WO2018/067813
PCT Pub. Date: Apr. 12, 2018

(65) Prior Publication Data
US 2019/0224377 A1 Jul. 25, 2019

Related U.S. Application Data

(60) Provisional application No. 62/404,627, filed on Oct. 5, 2016.

(51) Int. Cl.
*A61L 27/54* (2006.01)
*A61F 2/02* (2006.01)
(Continued)

(52) U.S. Cl.
CPC .............. *A61L 27/54* (2013.01); *A61F 2/022* (2013.01); *A61K 35/12* (2013.01); *A61K 35/13* (2013.01);
(Continued)

(58) Field of Classification Search
CPC ................. A61L 27/54; A61L 27/3683; A61L 2300/438; A61L 2300/64; A61F 2/022;
(Continued)

(56) References Cited

U.S. PATENT DOCUMENTS

| 4,902,476 A | 2/1990 | Gordon et al. |
| 5,169,390 A | 12/1992 | Athayde et al. |

(Continued)

FOREIGN PATENT DOCUMENTS

| EP | 1351623 B1 | 1/2005 |
| WO | WO2010061387 A2 | 6/2010 |

(Continued)

OTHER PUBLICATIONS

Papas et al, "Cultivation of Recombinant, Insulin-Secreting AtT-20 Cells as Free and Entrapped Spheroids," Cytotechnology, vol. 13, Jun. 1993, pp. 1-2.

(Continued)

*Primary Examiner* — Paul B Prebilic
(74) *Attorney, Agent, or Firm* — Sheridan Ross P.C.

(57) ABSTRACT

Methods, systems, and devices for enhancing cancer immunotherapy featuring co-transplantation of encapsulated xenogeneic cells with separately encapsulated autologous or allogeneic cells, e.g., autologous or allogeneic tumor cells. For example, both a first cellular transplantation device housing a patient's own tumor cells and a second cellular transplantation device housing xenogeneic cells may be implanted into a patient. The presence of the xenogeneic cells elicits an enhanced immune response, e.g., the xeno- (Continued)

geneic cells will draw in a large number of immune cells. Shed tumor antigens from the first cellular transplantation may then be taken up by the immune cells that were drawn to the xenogeneic cells. This will generate an anti-tumor immune response that is amplified relative to a response elicited by the encapsulated tumor cells alone.

16 Claims, 1 Drawing Sheet

(51) Int. Cl.

| | | |
|---|---|---|
| A61K 35/12 | (2015.01) | |
| A61K 35/13 | (2015.01) | |
| A61K 38/19 | (2006.01) | |
| A61K 39/39 | (2006.01) | |
| A61L 27/36 | (2006.01) | |
| A61P 35/00 | (2006.01) | |
| A61K 9/00 | (2006.01) | |
| A61K 39/00 | (2006.01) | |

(52) U.S. Cl.
CPC .............. *A61K 38/19* (2013.01); *A61K 39/39* (2013.01); *A61L 27/3683* (2013.01); *A61P 35/00* (2018.01); *A61K 9/0024* (2013.01); *A61K 2039/515* (2013.01)

(58) Field of Classification Search
CPC ..... A61F 2210/0076; A61F 2250/0068; A61K 35/13; A61K 2300/00
See application file for complete search history.

(56) References Cited

U.S. PATENT DOCUMENTS

| | | | |
|---|---|---|---|
| 5,324,518 | A | 6/1994 | Orth et al. |
| 5,368,028 | A | 11/1994 | Palti |
| 5,713,888 | A | 2/1998 | Neuenfeldt et al. |
| 5,741,330 | A | 4/1998 | Brauker et al. |
| 6,143,293 | A | 11/2000 | Weiss et al. |
| 6,156,305 | A | 12/2000 | Brauker et al. |
| 7,041,634 | B2* | 5/2006 | Weber ................. A61K 9/5073 424/93.7 |
| 7,892,222 | B2 | 2/2011 | Vardi et al. |
| 9,433,557 | B2 | 9/2016 | Green et al. |
| 11,446,133 | B2* | 9/2022 | Papas ..................... A61L 27/54 |
| 2002/0192190 | A1 | 12/2002 | Latta |
| 2003/0087427 | A1 | 5/2003 | Colton et al. |
| 2004/0166141 | A1 | 8/2004 | Cerami et al. |
| 2004/0197374 | A1 | 10/2004 | Rezania et al. |
| 2006/0013835 | A1 | 1/2006 | Anderson et al. |
| 2006/0019333 | A1 | 1/2006 | Rodgers et al. |
| 2006/0034812 | A1* | 2/2006 | Link, Jr. ................ A61K 38/45 514/44 R |
| 2007/0061015 | A1 | 3/2007 | Jensen et al. |
| 2010/0082114 | A1 | 4/2010 | Gingras et al. |
| 2010/0130916 | A1 | 5/2010 | Stern et al. |
| 2010/0196439 | A1 | 8/2010 | Beck et al. |
| 2010/0228110 | A1 | 9/2010 | Tsoukalis |
| 2010/0272771 | A1 | 10/2010 | Harlow et al. |
| 2011/0092949 | A1 | 4/2011 | Wang |
| 2014/0014226 | A1 | 1/2014 | Green et al. |
| 2014/0257515 | A1 | 9/2014 | So et al. |
| 2014/0308315 | A1 | 10/2014 | Knezevich et al. |
| 2015/0073381 | A1* | 3/2015 | Kauper ..................... A61P 1/16 604/93.01 |
| 2015/0112247 | A1 | 8/2015 | Tempelman et al. |
| 2015/0320836 | A1 | 11/2015 | Itkin-Ansari et al. |
| 2015/0359472 | A1 | 12/2015 | Botvinick et al. |
| 2016/0022180 | A1 | 1/2016 | Joseph et al. |
| 2016/0184569 | A1 | 6/2016 | Lathuiliere et al. |
| 2018/0201933 | A1* | 7/2018 | Cubillios-Ruiz .... C12N 15/113 |
| 2018/0369289 | A1* | 12/2018 | Lakey ................. A61K 31/025 |

FOREIGN PATENT DOCUMENTS

| | | |
|---|---|---|
| WO | WO2015145264 A2 | 10/2015 |
| WO | WO2018067813 A1 | 4/2018 |
| WO | WO2018085714 A1 | 5/2018 |
| WO | WO2018102077 A1 | 6/2018 |
| WO | WO2018144098 A1 | 8/2018 |
| WO | WO2018144099 A1 | 8/2018 |

OTHER PUBLICATIONS

Papas et al., "Development of a Bioartificial Pancreas: I. Long Term Propagation and Basal and Induced Secretion from Entrapped BTC3 Cell Cultures," Biotechnology and Bioengineering, vol. 66, No. 4, 1999, pp. 219-230.
Sambanis et al., "Towards the development of a bioartificial pancreas: immunoisolation and NMR monitoring of mouse insulinomas," Cytotechnology, vol. 15, 1994, pp. 351-363.
Wei et al., "Immunotherapy of tumors with xenogeneic endothelial cells as a vaccine," Nature Medicine, vol. 6, No. 10, Oct. 2000, pp. 1160-1166.
Extended European Search Report for European Patent Application No. 17859181.4, dated Apr. 24, 2020, 17 pages.
Lathuiliere et al. "Encapsulated Cellular Implants for Recombinant Protein Delivery and Therapeutic Modulation of the Immune System." International Journal of Molecular Sciences. May 2015 (May 8, 2015). vol. 16. pp. 10578-10600.
Lee et al. Cytokines in Cancer Immunotherapy. Cancers 2011, 3, 3856-3893.
Manickavasagam et al. Critical Assessment of Implantable Drug Delivery Devices in Glaucoma Management. Journal of Drug Delivery. vol. 2013, Article ID 895013, pp. 1-12.
Makadia et al. Poly Lactic-co-Glycolic Acid (PLGA) as Biodegradable Controlled Drug Delivery Carrier. Polymers (Basel). Sep. 1, 2011; 3(3): 1377-1397.
Gholipourmalekabadi et al. Oxygen-Generating Biomaterials: A New, Viable Paradigm for Tissue Engineering? Trends in Biotechnology, Dec. 2016, vol. 34, No. 12.
Geller et al. Use of an Immunoisolation Device for Cell Transplantation and Tumor Immunotherapy. Annals New York Academy of Sciences. pp. 438-451, (Dec. 17, 2006).
International Search Report for PCT Application No. PCT/US17/55334 dated Dec. 26, 2017.
Carlsson et al. Transplantation of macroencapsulated human islets within the bioartificial pancreas ßAir to patients with type 1 diabetes mellitus. Am J Transplant. 2018;18:1735-1744, (Feb. 2, 2018).
ViaCyte CEO Paul Laikind Interview: Trial Update, Melton's Concerns, & Future. https://ipscell.com/2015/03/viacyte/, (Mar. 2, 2015).
International Search Report for PCT Application No. PCT/US17/60036 dated Feb. 16, 2018.
International Search Report for PCT Application No. PCT/US17/60034 dated Jul. 12, 2018.
International Search Report for PCT Application No. PCT/US17/60041 dated Jul. 10, 2018.
International Search Report for PCT Application No. PCT/US17/60043 dated Jun. 14, 2018.
Hatfield et al., "Oxygenation to improve cancer vaccines, adoptive cell transfer and blockade of immunological negative regulators," OncoImmunology, vol. 4, No. 12, pp. e1052934-1-e1052934-3, (Jun. 2015).
Lee et al., "Hypoxia-Driven Immunosuppression: A new reason to use thermal therapy in the treatment of cancer?," International Journal of Hypothermia, vol. 26, No. 3, 2010, pp. 232-246.
Li et al., "Hypoxia-Driven immunosuppressive Metabolites in the Tumor Microenvironment: New Approaches for Combinational immunotherapy," Frontiers in Immunology, vol. 9, No. 1591, Jul. 2018, 12 pages.
Noman et al., "PD-L1 is a novel direct target of HIF-1a, and its blockade under hypoxia enhanced MDSC-mediated T cell activation," Journal of Experimental Medicine, vol. 211, No. 5, 2014, pp. 781-790.

(56) References Cited

OTHER PUBLICATIONS

Raa et al., "Hyperoxia retards growth and induces apoptosis and loss of glands and blood vessels in DMBA-induced rat mammary tumors," BMC Cancer, vol. 7, No. 23, Jan. 30, 2007, 10 pages.
Article 94(3) Communication for Europe Patent Application No. 17859181.4, dated Nov. 28, 2022, 9 pages.
Camci-Unal et al., "Oxygen-releasing biomaterials for tissue engineering," Polymer International, vol. 62, Apr. 2013, pp. 843-848.
Official Action for Canada Patent Application No. 3039653, dated Feb. 2, 2024, 8 pages.

* cited by examiner

METHODS AND SYSTEMS FOR AUGMENTING IMMUNE SYSTEM RESPONSES

CROSS REFERENCE

This application is a 371 and claims benefit of PCT/US17/55334, filed Oct. 5 2017, which claims priority to U.S. Patent Application No. 62/404,627, filed Oct. 5, 2016, the specification(s) of which is/are incorporated herein in their entirety by reference.

FIELD OF THE INVENTION

The present invention relates to methods, systems, and devices (e.g., implantable devices) for enhancing the immune system response for various purposes including but not limited to for enhancing cancer immunotherapy.

BACKGROUND OF THE INVENTION

Cancer vaccines have the potential to provide a personalized therapy that will attack a patient's cancer anywhere in the body and to treat cancers for which there is no effective current therapy. Cancers generally escape immune surveillance; however, if the immune system can be sensitized to tumor-associated antigens, the potential exists to develop personalized vaccines using antigens associated with a patient's own tumor.

The present invention features methods, systems, and devices for enhancing the immune system response for various purposes including but not limited to for enhancing cancer immunotherapy. The augmentation may be accomplished by co-transplantation of encapsulated xenogeneic cells with encapsulated autologous or allogeneic cells (e.g., autologous or allogeneic tumor cells). The methods, systems, and devices (e.g., implantable devices) of the present invention may feature the use of cytokines and/or other factors, e.g., oxygen, etc.

As an example, the present invention features methods and systems for generating a specific anti-tumor immune response. A first cellular transplantation device housing a patient's own tumor cells (or other appropriate cells) may be co-implanted with a second cellular transplantation device housing xenogeneic cells. Without wishing to limit the present invention to any theory or mechanism, it is believed that the presence of the xenogeneic cells will elicit an enhanced immune response, which will further strengthen the anti-tumor response. For example, molecules can escape from the cellular transplantation device, but cells cannot leave or enter the device. The xenogeneic antigens escaping from the second cellular transplantation may stimulate a potent immune response, resulting in accumulation of antigen presenting cells and a cytokine storm. The shed tumor antigens from the first cellular transplantation may then be taken up and presented by activated antigen presenting cells, thus generating an immune response that is further amplified relative to a response elicited by the encapsulated tumor cells alone.

SUMMARY OF THE INVENTION

The present invention features methods, systems, and devices for generating an immune response (e.g., a specific anti-tumor immune response). For example, the present invention features methods for enhancing or eliciting an anti-tumor immune response to a tumor cell (in a subject). The methods and systems of the present invention feature the use of implantable devices (e.g., a first cellular transplantation device, a second cellular transplantation device, etc.). A non-limiting example of an implantable device is a Theracyte™ device, an encapsulated device that protects allogeneic tissue from immune rejection without immunosuppression. Encapsulation devices may be vascularized, e.g., devices may be implanted for vascularization prior to loading cells through a port. In some embodiments, encapsulation devices are pre-implanted with controlled or slow-release microparticles without cells. Cells may be introduced about 2-4 weeks after implantation, e.g., after blood vessels have formed around the device (to enhance chances that factors released by the implanted cells reach their target). (See Manickavasagam and Oyewumi, 2013, Journal of Drug Delivery 2013:1-12.) Encapsulation devices may be retrievable.

In some embodiments, the method comprises implanting (in the subject) a first cellular transplantation device housing an allogeneic or autologous tumor cells (or a combination thereof) surrounded by a cell impermeable membrane and a second cellular transplantation device housing xenogeneic cells surrounded by a cell impermeable membrane. The tumor cells may be living or irradiated to render them non-proliferating or a combination thereof. The tumor cells secrete tumor antigens through the cell impermeable membrane, and the xenogeneic cells secrete xenogeneic antigens through the cell impermeable membrane. Immune cells are drawn to the second cellular transplantation device (drawn to the xenogeneic antigens). The immune cells drawn to the second cellular transplantation device (drawn to the xenogeneic antigens) are exposed to the tumor antigens secreted by the tumor cells in the first cellular transplantation device, and the immune cells activate an anti-tumor immune response targeted to the tumor cells in the first cellular transplantation device.

As discussed below, the cellular transplantation devices (encapsulation devices) may be pre-implanted without cells. Cells may be introduced at a particular time point after implantation (e.g., about 2-4 weeks after implantation, days later, 1 week later, 2 weeks later, 3 weeks later, 4 weeks later, 5 weeks later, a time point between 1 to 5 weeks, etc.), e.g., after blood vessels have formed around the device.

As discussed below, in some embodiments, the cellular transplantation devices (encapsulation devices) are pre-implanted with controlled or slow-release microparticles (without cells), e.g., the cellular transplantation devices feature components (e.g., microparticles) that are adapted for controlled release of certain factors (e.g., cytokines). Or, the cellular transplantation devices may feature cells (e.g., specific cells, engineered cells) that produce certain factors.

As discussed below, factors, e.g., cytokines that can be implanted (e.g., via a controlled release system, via a cell, via an engineered cell, etc.) released include but are not limited to: IL-2, GM-CSF, G-CSF, IL-1, IL-3, IL-4, IL-5, IL-6, IL-7, IL-8, IL-10, IL-12, IL-15, IL-18, IL-21, IL-23, IFN-gamma, TGF-beta, TNF-alpha, IL-9, IL-13, IL-27, erythropoietin, growth hormone, prolactin, oncostatin M, leukemia inhibitory factor, IFN-alpha/beta, IL-20, IL-22, IL-28, CSF1, c-kit, IL-7, IL-17B, IL-17C, IL-17D, IL-17E, IL-17F, CC chemokines, CXC chemokine, CD27, CD30, CD40, CD120, lymphotoxin-beta, etc.

In some embodiments, the second cellular transplantation device is implanted adjacent to the first cellular transplantation device. In some embodiments, the second cellular transplantation device is implanted near the first cellular transplantation device. In some embodiments, the anti-tumor immune response is enhanced as compared to an anti-tumor immune response elicited by implantation of the first cellular transplantation device alone. In some embodiments, more than one first cellular transplantation device is implanted. In some embodiments, more than one second cellular transplantation device is implanted. In some embodiments, the cellular transplantation devices are separate compartments within a single device container. In some embodiments, the cellular transplantation devices are implanted subcutaneously. In some embodiments, the first cellular transplantation device is operatively connected to an exogenous oxygen generator. In some embodiments, the xenogeneic cells are cells of any species other than human. In some embodiments, the xenogeneic cells are porcine cells, rat cells, mouse cells, goat cells, rabbit cells, or a combination thereof.

The present invention also features a system comprising a first cellular transplantation device and a second cellular transplantation device. The system may be implanted into a subject. In some embodiments, the cellular transplantation devices are adjacent to one another or near one another.

For example, the present invention features a system comprising a first cellular transplantation device housing tumor cells surrounded by a cell impermeable membrane; and a second cellular transplantation device housing xenogeneic cells surrounded by a cell impermeable membrane. In some embodiments, the tumor cells comprise allogeneic tumor cells, autologous tumor cells, or a combination thereof. In some embodiments, the tumor cells are living, irradiated to render them non-proliferating, or a combination thereof. The tumor cells secrete tumor antigens through the cell impermeable membrane. The xenogeneic cells secrete xenogeneic antigens through the cell impermeable membrane. In some embodiments, the first cellular transplantation device and the second cellular transplantation device are adjacent to each other. In some embodiments, the first cellular transplantation device and the second cellular transplantation device are stacked atop one another. In some embodiments, the first cellular transplantation device and the second cellular transplantation device are a distance apart. In some embodiments, the first cellular transplantation device and the second cellular transplantation device are contained within a device container. In some embodiments, a barrier separates the first cellular transplantation device and the second cellular transplantation device contained within the device container. In some embodiments, the system further comprises one or more additional first cellular transplantation devices. In some embodiments, the system further comprises one or more additional second cellular transplantation devices.

The present invention also features a device container comprising a first cellular transplantation device and a second cellular transplantation device. The present invention also features a device container comprising one or more first cellular transplantation devices and one or more second cellular transplantation devices.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

The features and advantages of the present invention will become apparent from a consideration of the following detailed description presented in connection with the accompanying drawings in which.

DETAILED DESCRIPTION OF THE INVENTION

The present invention features methods, systems, and devices for enhancing the immune system response for various purposes including but not limited to for enhancing cancer immunotherapy. The augmentation may be accomplished by co-transplantation of encapsulated xenogeneic cells with encapsulated autologous or allogeneic cells (e.g., autologous or allogeneic tumor cells).

Figure 1:
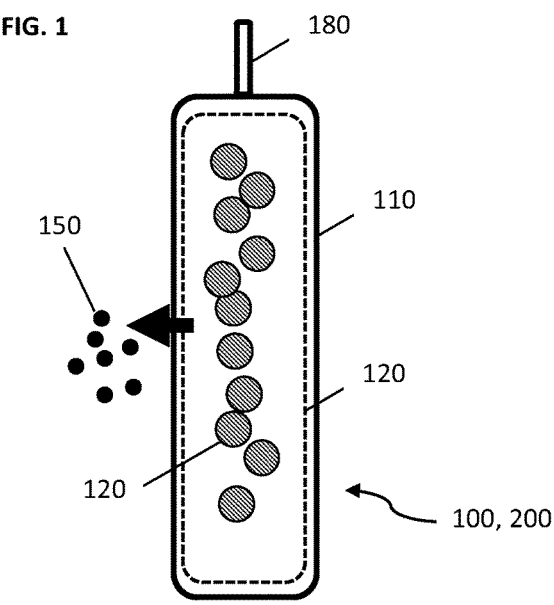
FIG. 1 shows a non-limiting example of a cellular transplantation device of the present invention.

As shown in FIG. 1 and as described above, the present invention features methods and systems for generating an enhanced anti-tumor immune response. For example, as shown in FIG. 1, a cellular transplantation device (100, 200) comprises cells (105), e.g., allogeneic cells or autologous cells in one example (device 100), xenogeneic cells in another example (device 200). The cellular transplantation device (100, 200) comprises a membrane (e.g., an inner membrane (120)) that is impermeable to cells. Non-cell factors or molecules (150), such as xenogeneic factors or antigens in the device (200) housing the xenogeneic cells, can escape the cell impermeable membrane. In some embodiments, the device (100, 200) comprises an outer membrane (110). In some embodiments, the device (100, 200) comprises a loading port (180).

In some embodiments, other molecules or components are housed with the cells (105). For example, in some embodiments, the system comprises slow-releasing molecules, microspheres, or other compounds housed with the cells (105).

As previously discussed, the cellular transplantation devices (encapsulation devices) may be pre-implanted without cells. Cells may be introduced at a particular time point after implantation (e.g., about 2-4 weeks after implantation, days later, 1 week later, 2 weeks later, 3 weeks later, 4 weeks later, 5 weeks later, a time point between 1 to 5 weeks, etc.), e.g., after blood vessels have formed around the device. Without wishing to limit the present invention to any theory or mechanism, blood vessel formation around the device may help to enhance the chances that factors released by the implanted cells reach their target.

In some embodiments, the cellular transplantation devices (encapsulation devices) are pre-implanted with controlled or slow-release microparticles (without cells), e.g., the cellular transplantation devices feature components (e.g., microparticles) that are adapted for controlled release of certain factors (e.g., cytokines). Or, the cellular transplantation devices may feature cells (e.g., specific cells, engineered cells) that produce certain factors. Without wishing to limit the present invention to any theory or mechanism, secreting such factors specifically from cells implanted may be more advantageous than just releasing them through particles. For example, a longer release system may be created from cells that produce the factors and release them perhaps indefinitely), whereas the release of factors with slow releasing particles is limited to the amount originally contained in the particles.

Various appropriate biomaterials may be considered for the microparticles. As a non-limiting example, slow release particles may comprise liposomes (e.g., as described in Geller et al., 1997, Ann NY Acad Sci 831:438-451), a fibrin sealant, alginate based beads, Poly Lactic-co-Glycolic Acid (PLGA), etc. (see Makadia and Siegel, 2011, Polymers 3(3):1377-1397).

Factors, e.g., cytokines that can be released include (but are not limited to) IL-2, GM-CSF, G-CSF, IL-1, IL-3, IL-4, IL-5, IL-6, IL-7, IL-8, IL-10, IL-12, IL-15, IL-18, IL-21, IL-23, IFN-gamma, TGF-beta, TNF-alpha, IL-9, IL-13, IL-27, erythropoietin, growth hormone, prolactin, oncostatin M, leukemia inhibitory factor, IFN-alpha/beta, IL-20, IL-22, IL-28, CSF1, c-kit, IL-7, IL-17B, IL-17C, IL-17D, IL-17E, IL-17F, CC chemokines, CXC chemokine, CD27, CD30, CD40, CD120, lymphotoxin-beta, etc. (see Tables 1 and 2 of Lee and Margolin, 2011, Cytokines in Cancer Immunotherapy, 3(4):3856-3893. As previously discussed, cells can be engineered to secrete these specific factors at high levels and can be implanted in devices to do so and further enhance the response.

In some embodiments, a first cellular transplantation device (100) housing allogeneic or autologous cells (e.g., a patient's own tumor cells) or other appropriate cells are co-implanted with a second cellular transplantation device (200) housing xenogeneic cells. In some embodiments, the two devices (100, 200) are co-implanted such that they are adjacent to each other (e.g., next to, stacked atop one another, etc.). In some embodiments, the two devices (100, 200) are co-implanted such that they are near each other. In some embodiments, the two devices (100, 200) are co-implanted such that they are far from each other. In some embodiments, the two devices (100, 200) are combined as a single device with two separate compartments (e.g., the two devices (100, 200) are effectively housed in a larger device). FIG. 2 shows various non-limiting example of configurations of devices implanted near or adjacent to each other.

Without wishing to limit the present invention to any theory or mechanism, it is believed that the presence of the xenogeneic cells (in the second cellular transplantation device (200)) will elicit an enhanced immune response. Geller et al. (Ann NY Acad Sci, 1997, 831:438-451) discusses attempts at reducing an immune response elicited by a xenograft (alleging the immune response is undesired); the present invention uses the immune response elicited by the xenograft to expose the autologous/allogeneic tumor cells to even more immune cells, e.g., to enhance the anti-tumor response.

In some embodiments, more than one first cellular transplantation device (100) is implanted, e.g., two allogeneic and/or autologous devices are used, three allogeneic and/or autologous devices are used, four allogeneic and/or autologous devices are used, etc. In some embodiments, more than one second cellular transplantation device (200) is implanted, e.g., two xenogeneic devices are used, three xenogeneic devices are used, four xenogeneic devices are used, etc.

Figure 2A:
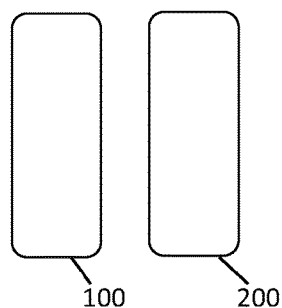
FIG. 2A shows two separate transplantation devices for implantation.
Figure 2B:
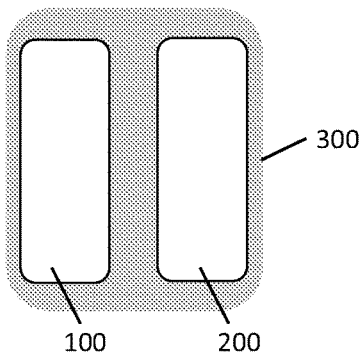
FIG. 2B shows two separate transplantation devices as two separate compartments in a single device.
Figure 2C:
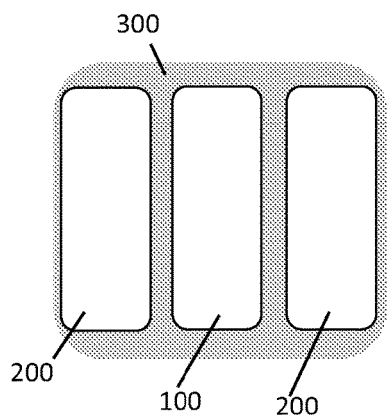
FIG. 2C shows three separate transplantation devices as three separate compartments in a single device.
Figure 2D:
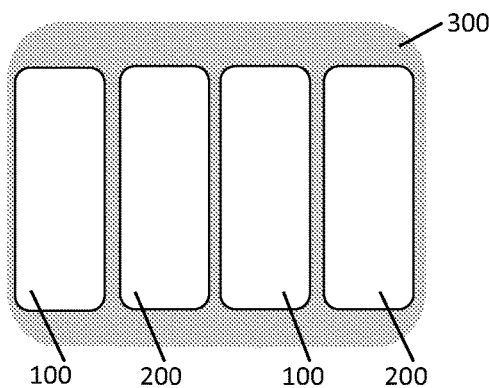
FIG. 2D shows four separate transplantation devices as four separate compartments in a single device.
Figure 2E:
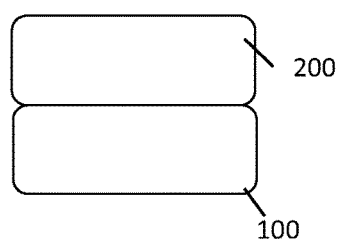
FIG. 2E shows two transplantation devices stacked atop one another.
Figure 2F:
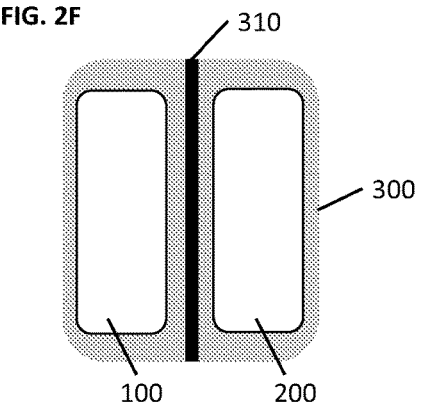
FIG. 2F shows two transplantation devices separated by a barrier (310).

In some embodiments, the devices are stacked. In some embodiments, the stacked device comprises two compartments. In some embodiments, the stacked device comprises four compartments. In some embodiments, the stacked device comprises more than four compartments. In some embodiments, the xenogeneic cells are sandwiched between autologous and/or allogeneic cells. In some embodiments, the autologous and/or allogeneic cells are sandwiched between xenogeneic cells. Any appropriate combination of cells may be used and stacked as appropriate. FIG. 2A shows two separate transplantation devices (100, 200) for implantation. FIG. 2B shows two separate transplantation devices (100, 200) as two separate compartments in a single device container (300). FIG. 2C shows three separate transplantation devices as three separate compartments in a single device container (300). FIG. 2D shows four separate transplantation devices as four separate compartments in a single device container (300). FIG. 2E shows two transplantation devices stacked atop one another. FIG. 2F shows two transplantation devices separated by a barrier (310), e.g., the device container is split into two compartments. The present invention is not limited to the combinations of first cellular transplantation devices (100) and/or second cellular transplantation devices (200) described herein or shown in FIG. 2A, FIG. 2B, FIG. 2C, FIG. 2C, FIG. 2E, or FIG. 2F. Any other configuration or combination of configurations may be considered. As previously discussed, the compartments may house a combination of xenogeneic and allogeneic and/or autologous cells arranged as appropriate.

As previously discussed, the xenogeneic-driven immune response may help strengthen the anti-tumor response elicited by the cells in the first cellular transplantation device (100), e.g., the allogeneic or autologous cells (e.g., the patient's own tumor cells). For example, molecules (105) can escape from the cellular transplantation devices (100, 200), but cells (105) cannot leave or enter the devices. The xenogeneic antigens (105) escaping from the second cellular transplantation device (200) may stimulate a potent immune response, resulting in accumulation of antigen presenting cells and a cytokine storm. The shed tumor antigens from the first cellular transplantation device (100) may then be taken up and presented by activated antigen presenting cells, thus generating an immune response that is further amplified relative to a response elicited by the encapsulated tumor cells alone.

The present invention is not limited to applications involving tumor cells.

In some embodiments, the transplantation devices are implanted subcutaneously. The present invention is not limited to subcutaneous implantation.

The xenogeneic cells (e.g., when implanted in humans) are any cells other than human cells. In some embodiments, the xenogeneic cells are porcine cells, rat cells, mouse cells, goat cells, rabbit cells, or any other appropriate cell type (e.g., bacterial cells, fungal cells, other mammalian cells, etc.).

In some embodiments, the cells, e.g., tumor cells, in the device are living or irradiated (e.g., to render non-proliferating), or a combination thereof. Without wishing to limit the present invention to any theory or mechanism, it is believed that irradiation may enhance the release of antigen from the tumor cells early on. In some embodiments, if a combination of non-irradiated and irradiated cells are used, the irradiated cells may release antigen early and the living/ proliferating non-irradiated cells may continue to release antigen for a longer period of time.

In some embodiments, the present invention features delivery of exogenous oxygen. Oxygen may be delivered, for example, from an oxygen generator. Oxygen may be delivered via oxygen generating biomaterials (e.g., calciumperoxide, magnesiumperoxide, sodiumpercarbonate), see Gholipourmalekabadi et al., 2016, Trends in Biotechnology 34(12):1010-1021. Such biomaterials may be added in microspheres/polymeric particles within devices and deliver oxygen to cells in the transplantation devices.

As previously discussed, the present invention features methods for enhancing an immune response in a subject. In some embodiments, the method comprises implanting in the subject a cellular transplantation device housing xenogeneic cells surrounded by a cell impermeable membrane wherein the xenogeneic cells secrete xenogeneic antigens through the cell impermeable membrane and immune cells of the subject are drawn to the cellular transplantation device. In some embodiments, the method comprises implanting in the subject a cellular transplantation device comprising an inner compartment surrounded by a cell impermeable membrane; and introducing xenogeneic cells into the inner compartment of the cellular transplantation device after a period of time, wherein the xenogeneic cells secrete xenogeneic antigens through the cell impermeable membrane and immune cells of the subject are drawn to the cellular transplantation device. In some embodiments, the method comprises implanting in the subject a cellular transplantation device housing cells surrounded by a cell impermeable membrane wherein the cells secrete antigens through the cell impermeable membrane and immune cells of the subject are drawn to the cellular transplantation device. In some embodiments, the method comprises implanting in the subject a cellular transplantation device comprising an inner compartment surrounded by a cell impermeable membrane; and introducing cells into the inner compartment of the cellular transplantation device after a period of time, wherein the cells secrete antigens through the cell impermeable membrane and immune cells of the subject are drawn to the cellular transplantation device. In some embodiments, the method comprises implanting in the subject a first cellular transplantation device comprising an inner compartment surrounded by a cell impermeable membrane; implanting in the subject a second cellular transplantation device comprising an inner compartment surrounded by a cell impermeable membrane; introducing cells into the inner compartment of the first cellular transplantation device after a period of time, wherein the cells secrete antigens through the cell impermeable membrane; and introducing xenogeneic cells into the inner compartment of the second cellular transplantation device after a period of time, wherein the xenogeneic cells secrete xenogeneic antigens through the cell impermeable membrane and immune cells are drawn to the second cellular transplantation device. In some embodiments, the method comprises implanting in the subject a first cellular transplantation device housing cells surrounded by a cell impermeable membrane, wherein the cells secrete antigens through the cell impermeable membrane; and implanting in the subject a second cellular transplantation device housing xenogeneic cells surrounded by a cell impermeable membrane, wherein the xenogeneic cells secrete xenogeneic antigens through the cell impermeable membrane and immune cells are drawn to the second cellular transplantation device.

The immune cells drawn to the second cellular transplantation device are exposed to the antigens secreted by the cells in the first cellular transplantation device and the immune cells target the cells in the first cellular transplantation device.

The present invention also features a method of enhancing an anti-tumor immune response to a tumor cell in a subject. In some embodiments, the method comprises implanting in the subject a first cellular transplantation device comprising an inner compartment surrounded by a cell impermeable membrane; implanting in the subject a second cellular transplantation device comprising an inner compartment surrounded by a cell impermeable membrane; introducing tumor cells into the inner compartment of the first cellular transplantation device after a period of time, wherein the tumor cells secrete tumor antigens through the cell impermeable membrane; and introducing xenogeneic cells into the inner compartment of the second cellular transplantation device after a period of time, wherein the xenogeneic cells secrete xenogeneic antigens through the cell impermeable membrane and immune cells are drawn to the second cellular transplantation device. In some embodiments, the method comprises implanting in the subject a first cellular transplantation device housing tumor cells surrounded by a cell impermeable membrane, wherein the tumor cells secrete tumor antigens through the cell impermeable membrane; and implanting in the subject a second cellular transplantation device housing xenogeneic cells surrounded by a cell impermeable membrane, wherein the xenogeneic cells secrete xenogeneic antigens through the cell impermeable membrane and immune cells are drawn to the second cellular transplantation device. The immune cells drawn to the second cellular transplantation device are exposed to the tumor antigens secreted by the tumor cells in the first cellular transplantation device and the immune cells activate an anti-tumor immune response targeted to the tumor cells in the first cellular transplantation device.

The tumor cells may comprise allogeneic tumor cells, autologous tumor cells, or a combination thereof. The tumor cells may be living, irradiated to render them non-proliferating, or a combination thereof.

The cells in the cellular transplantation device may be cells of any cell type. In some embodiments, the first cellular transplantation device and the second cellular transplantation device are implanted at the same time.

In some embodiments, the tumor cells are implanted in the first cellular transplantation device and the xenogeneic cells are implanted in the second cellular transplantation device at the same time.

The cells (or controlled release molecules, as discussed below) may be introduced to the respective cellular transplantation devices via a port in the cellular transplantation devices.

In some embodiments, the first cellular transplantation device and the second cellular transplantation device are connected. In some embodiments, the first cellular transplantation device and the second cellular transplantation device are housed within a single housing. In some embodiments, the first cellular transplantation device and the second cellular transplantation device are separate. In some embodiments, the first cellular transplantation device and the second cellular transplantation device are stacked.

The present invention may feature the use of molecules such as controlled release particles that allow for the controlled release of compounds such as bioagents, e.g., cytokines. Controlled release molecules may be added with the cells, or they may be introduced after the cells have been introduced to the cellular transplantation devices. They may be added at different time points prior to the introduction of cells. They may be implanted with cells (without pre-implantation of the device), etc.

In some embodiments, the bioagent comprises a cytokine. In some embodiments, the cytokine comprises IL-1, IL-2, IL-3, IL-4, IL-5, IL-6, IL-7, IL-8, IL-9, IL-10, IL-12, IL-13, IL-15, IL-17, IL-17B, IL-17C, IL-17D, IL-17E, IL-17F, IL-18, IL-20, IL-21, IL-22, IL-23, IL-27, IL-28, GM-CSF, G-CSF, IFN-gamma, TGF-beta, TNF-alpha, erythropoietin, growth hormone, prolactin, oncostatin M, leukemia inhibitory factor, IFN-alpha/beta, CSF1, c-kit, CC chemokines, CXC chemokine, CD27, CD30, CD40, CD120, lymphotoxin-beta, or a combination thereof.

In some embodiments, the cellular transplantation device further comprises controlled release particles for controlled release of a bioagent. In some embodiments, the first cellular transplantation device, the second cellular transplantation device, or both the first cellular transplantation device and the second cellular transplantation device comprise controlled release particles for controlled release of a bioagent. In some embodiments, the controlled release particles are introduced to the cellular transplantation device after the cells are introduced to the cellular transplantation device. In some embodiments, the controlled release particles are introduced to the first cellular transplantation device, the second cellular transplantation device, or both the first cellular transplantation device and the second cellular transplantation device after cells are introduced to the respective cellular transplantation device. In some embodiments, the controlled release particles and the cells are implanted at the same time. In some embodiments, the controlled release particles are introduced prior to the cells.

In some embodiments, the cells (e.g., cells, the tumor cells, xenogeneic cells, or both the tumor cells and xenogeneic cells, etc.) are introduced to the cellular transplantation device at a time point from 1 day to 5 weeks after implantation. In some embodiments, the cells (e.g., cells, the tumor cells, xenogeneic cells, or both the tumor cells and xenogeneic cells, etc.) are introduced to the cellular transplantation device at a time point from 2 to 4 weeks after implantation.

In some embodiments, oxygen is delivered to the cellular transplantation device. In some embodiments, oxygen is delivered to the cellular transplantation device via an oxygen generating biomaterial (e.g., calciumperoxide, magnesiumperoxide, sodiumpercarbonate, or a combination thereof).

In some embodiments, the anti-tumor immune response is enhanced as compared to an anti-tumor immune response elicited by implantation of the first cellular transplantation device with tumor cells alone.

In some embodiments, more than one first cellular transplantation device with cells is implanted. In some embodiments, more than one second cellular transplantation device with cells is implanted. In some embodiments, one or more of the cellular transplantation devices are implanted subcutaneously.

The xenogeneic cells may be cells of any species other than human, e.g., porcine cells, rat cells, mouse cells, goat cells, rabbit cells, or a combination thereof.

As previously discussed, the present invention also features system, e.g., cellular transplantation devices. In some embodiments, the system comprises a cellular transplantation device housing xenogeneic cells surrounded by a cell impermeable membrane, wherein the xenogeneic cells secrete xenogeneic antigens through the cell impermeable membrane. In some embodiments, the system comprises a first cellular transplantation device housing tumor cells surrounded by a cell impermeable membrane, wherein the tumor cells secrete tumor antigens through the cell impermeable membrane; and a second cellular transplantation device housing xenogeneic cells surrounded by a cell impermeable membrane, wherein the xenogeneic cells secrete xenogeneic antigens through the cell impermeable membrane.

The tumor cells may comprise allogeneic tumor cells, autologous tumor cells, or a combination thereof. The tumor cells may be living, irradiated to render them non-proliferating, or a combination thereof.

In some embodiments, the first cellular transplantation device and the second cellular transplantation device are connected. In some embodiments, the first cellular transplantation device and the second cellular transplantation device are housed within a single housing. In some embodiments, a barrier separates the first cellular transplantation device and the second cellular transplantation device contained within the single housing. In some embodiments, the first cellular transplantation device and the second cellular transplantation device are separate. In some embodiments, the first cellular transplantation device and the second cellular transplantation device are stacked.

As previously discussed, in some embodiments, the cellular transplantation device further comprises controlled release particles for controlled release of a bioagent. In some embodiments, the first cellular transplantation device, the second cellular transplantation device, or both the first cellular transplantation device further comprise controlled release particles for controlled release of a bioagent, e.g., as described above.

In some embodiments, the system further comprises a system for delivering oxygen to the cellular transplantation device. In some embodiments, the system for delivering oxygen comprises an oxygen generating biomaterial. In some embodiments, the oxygen generating biomaterial comprises calciumperoxide, magnesiumperoxide, sodiumpercarbonate, or a combination thereof.

In some embodiments, the xenogeneic cells may be cells of any species other than human. In some embodiments, the xenogeneic cells are porcine cells, rat cells, mouse cells, goat cells, rabbit cells, or a combination thereof.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A method of providing an anti-tumor immune response to a tumor cell in a subject, said method comprising:
   a. implanting in the subject a first cellular transplantation device comprising an inner membrane and an outer membrane; wherein the inner membrane is impermeable to cells and permeable to molecules, wherein the first cellular transplantation devices comprises allogeneic tumor cells housed within the inner membrane, autologous tumor cells, or a combination thereof, wherein the cells secrete antigens through the inner membrane; and
   b. implanting in the subject a second cellular transplantation device comprising an inner membrane and an outer membrane; wherein the inner membrane is impermeable to cells and permeable to molecules, wherein the second cellular transplantation device comprises xenogeneic cells housed within the inner membrane that secrete xenogeneic antigens through the inner membrane and immune cells are drawn to the second cellular transplantation device;
   wherein the immune cells drawn to the second cellular transplantation device are exposed to the tumor antigens secreted by the cells in the first cellular transplantation device and the immune cells activate and/or enhance an anti-tumor response targeted to the cells in the first cellular transplantation device.

2. The method of claim 1, wherein the first cellular transplantation device and the second cellular transplantation device are stacked.

3. The method of claim 1, wherein the first cellular transplantation device and the second cellular transplantation device are connected.

4. The method of claim 1, wherein the first cellular transplantation device and the second cellular transplantation device are housed within a single housing.

5. The method of claim 2, wherein the first cellular transplantation device and the second cellular transplantation device are connected.

6. The method of claim 2, wherein the first cellular transplantation device and the second cellular transplantation device are housed within a single housing.

7. The method of claim 1, wherein oxygen is delivered to at least one of the first cellular transplantation device and the second cellular transplantation device.

8. The method of claim 2, wherein oxygen is delivered to at least one of the first cellular transplantation device and the second cellular transplantation device.

9. The method of claim 1, wherein more than one first cellular transplantation device with cells is implanted.

10. The method of claim 1, wherein more than one second cellular transplantation device with cells is implanted.

11. The method of claim 2, wherein more than one first cellular transplantation device with cells is implanted.

12. The method of claim 2, wherein more than one second cellular transplantation device with cells is implanted.

13. A method of providing an anti-tumor immune response to a tumor cell in a subject, said method comprising:
   a. implanting in the subject a first cellular transplantation device comprising an inner membrane and an outer membrane; wherein the inner membrane surrounds tumor cells and is impermeable to cells and permeable to molecules, wherein the cells in the first cellular transplantation device comprise allogeneic tumor cells, autologous tumor cells, or a combination thereof, wherein the cells secrete tumor antigens through the inner membrane membrane; and
   b. implanting in the subject a second cellular transplantation device comprising an inner membrane and an outer membrane; wherein the inner membrane surrounds at least one bioagent and is impermeable to cells and permeable to molecules, wherein the bioagent is secreted through the inner membrane and immune cells are drawn to the second cellular transplantation device;
   wherein the first cellular transplantation device and the second cellular transplantation device are connected, are stacked, and are housed within a single housing;
   wherein oxygen is delivered to at least one of the first cellular transplantation device and the second cellular transplantation device; and
   wherein the at least one bioagent is selected from the group consisting of IL-1, IL-2, IL-3, IL-4, IL-5, IL-6, IL-7, IL-8, IL-9, IL-10, IL-12, IL-13, IL-15, IL-17, IL-17B, IL-17C, IL-17D, IL-17E, IL-17F, IL-18, IL-20, IL-21, IL-22, IL-23, IL-27, IL-28, GM-CSF, G-CSF, IFN-gamma, TGF-beta, TNF-alpha, erythropoietin, growth hormone, prolactin, oncostatin M, leukemia inhibitory factor, IFN-alpha/beta, CSF1, c-kit, CC chemokines, CXC chemokine, CD27, CD30, CD40, CD120, lymphotoxin-beta, or a combination thereof; and
   wherein the immune cells drawn to the second cellular transplantation device are exposed to the tumor antigens secreted by the cells in the first cellular transplantation device and the immune cells activate and/or enhance an anti-tumor response targeted to the cells in the first cellular transplantation device.

14. The method of claim 13, wherein oxygen is delivered to the first cellular transplantation device and the second cellular transplantation device.

15. The method of claim 13, wherein more than one first cellular transplantation device is implanted.

16. The method of claim 13, wherein more than one second cellular transplantation device is implanted.

* * * * *